(12) United States Patent
Nakashima et al.

(10) Patent No.: US 7,940,975 B2
(45) Date of Patent: May 10, 2011

(54) MEDICAL IMAGE DIAGNOSING SUPPORT METHOD AND APPARATUS, AND IMAGE PROCESSING PROGRAM CONFIGURED TO EXTRACT AND CORRECT LESION CANDIDATE REGION

(75) Inventors: Kuniyoshi Nakashima, Kashiwa (JP); Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 967 days.

(21) Appl. No.: 11/658,617

(22) PCT Filed: Jul. 28, 2005

(86) PCT No.: PCT/JP2005/013819
§ 371 (c)(1),
(2), (4) Date: Jan. 25, 2007

(87) PCT Pub. No.: WO2006/011545
PCT Pub. Date: Feb. 2, 2006

(65) Prior Publication Data
US 2008/0298658 A1    Dec. 4, 2008

(30) Foreign Application Priority Data
Jul. 30, 2004  (JP) ................................. 2004-222711

(51) Int. Cl.
*G06K 9/00* (2006.01)
(52) U.S. Cl. ........................................................ 382/131
(58) Field of Classification Search .......... 382/128–134; 128/920–930; 356/39–49; 600/407–414, 600/424–426
See application file for complete search history.

(56) References Cited

U.S. PATENT DOCUMENTS

| 5,319,551 A | 6/1994 | Sekiguchi et al. |
| 5,732,121 A | 3/1998 | Takeo et al. |
| 6,363,163 B1 * | 3/2002 | Xu et al. ........................ 382/130 |
| 6,463,167 B1 * | 10/2002 | Feldman et al. ............... 382/128 |
| 2002/0009215 A1 * | 1/2002 | Armato et al. ................. 382/131 |

(Continued)

FOREIGN PATENT DOCUMENTS

JP     8-110939     4/1996

(Continued)

OTHER PUBLICATIONS

Machine Translation for JPN 2003010171 submitted in IDS Jan. 25, 2007 and present in IFW.*
International Preliminary Report on Patentability in connection with PCT/JP2005/013819.

*Primary Examiner* — Samir A. Ahmed
*Assistant Examiner* — Atiba O Fitzpatrick
(74) *Attorney, Agent, or Firm* — Cooper & Dunham LLP (57) ABSTRACT

A medical image diagnosing support method is provided that includes a site region extracting step for obtaining a tomographic image which is picked up by a medical diagnostic imaging apparatus and extracting a predetermined site region from the obtained tomographic image, a first region extracting step for extracting a first lesion candidate region from the site region based on pixel values of the site region extracted in the predetermined site region extracting step, a second region extracting step for extracting a second lesion candidate region from the site region based on a distribution of the pixel values of the site region extracted in the predetermined site region extracting step, and a region correcting step for correcting the first lesion candidate region extracted in the first region extracting step by using the second lesion candidate region extracted in the second region extracting step.

20 Claims, 10 Drawing Sheets

U.S. PATENT DOCUMENTS

| | | |
|---|---|---|
| 2003/0018245 A1 | 1/2003 | Kaufman et al. |
| 2003/0103665 A1 | 6/2003 | Uppaluri et al. |
| 2003/0179915 A1 | 9/2003 | Goto |
| 2004/0086162 A1 | 5/2004 | Doi et al. |
| 2004/0101089 A1 | 5/2004 | Karau et al. |
| 2004/0120561 A1 * | 6/2004 | Goto ............... 382/128 |
| 2006/0050943 A1 | 3/2006 | Ozaki et al. |

FOREIGN PATENT DOCUMENTS

| | | |
|---|---|---|
| JP | 9-167238 | 6/1997 |
| JP | 2845995 | 1/1999 |
| JP | 2003-10171 | 1/2003 |
| JP | 2003-70781 | 3/2003 |
| JP | 2004-180932 | 7/2004 |

* cited by examiner

FIG. 11(a)
OUTER SURFACE

FIG. 11(b)
INNER SURFACE

FIG. 11(c)
DIAPHRAGM SURFACE

MEDICAL IMAGE DIAGNOSING SUPPORT METHOD AND APPARATUS, AND IMAGE PROCESSING PROGRAM CONFIGURED TO EXTRACT AND CORRECT LESION CANDIDATE REGION

TECHNICAL FIELD

The present invention relates to a medical image diagnosing support method and apparatus for accurately displaying a progression of pulmonary emphysema.

The present application claims the benefit of the priority under the Paris Convention based on a Japanese Patent Application No. 2004-222711 according to Japanese Patent Law, and claims the benefit of the Japanese Patent Application No. 2004-222711 which is incorporated herein by reference.

BACKGROUND ART

Pulmonary emphysema is a disease featured by the irreversible progression after occurrence. So it is an important technology that can provide image diagnosing information which allows an early detection of pulmonary emphysema and an assessment of progression of the pulmonary emphysema, to doctors.

Actually, an image diagnosing technology for assessing a progression of pulmonary emphysema includes: extracting a lung field region and a pulmonary emphysema region from a tomographic image having the entire lung field region based on thresholds; calculating a ratio of the pulmonary emphysema region to the entire lung field region; and displaying the outer contour of the pulmonary emphysema region in different colors depending on the value of the ratio so that the progression of pulmonary emphysema can be intuitively understood (for example, see Japanese Patent Application Laid-Open No. 2003-10171).

Patent Document: Japanese Patent Application Laid-Open No. 2003-10171

However, in the extraction method disclosed in the Japanese Patent Application Laid-Open No. 2003-10171, there is a possibility of an excess extraction since extra several pixels are extracted to be added to the original size of a pulmonary emphysema region. That is, the Japanese Patent Application Laid-Open No. 2003-10171 was made without consideration for enhancing accuracy in extracting a pulmonary emphysema region.

In an aspect of this disclosure, there is provided a medical image diagnosing support method and apparatus, and an image processing program which can achieve improved accuracy in extracting a pulmonary emphysema region.

In another aspect of this disclosure, there is provided a medical image diagnosing support method that includes: a site region extracting step for obtaining a tomographic image which is picked up by a medical image diagnosing apparatus and extracting a predetermined site region from the obtained tomographic image; a first region extracting step for extracting a first lesion candidate region from the site region based on pixel values of the site region extracted in the predetermined site region extracting step; a second region extracting step for extracting a second lesion candidate region from the site region based on a distribution of the pixel values of the site region extracted in the predetermined site region extracting step; and a region correcting step for correcting the first lesion candidate region extracted in the first region extracting step by using the second lesion candidate region extracted in the second region extracting step.

The predetermined site is preferably the lung, and the lesion candidate is preferably the pulmonary emphysema herein. However, since the site may be lumen organs such as the enteric canal, and the lesion candidate may be applied to detect cancer cells, the term "predetermined site" and the term "lesion candidate" are used herein.

In another aspect, there is provided a medical image diagnosing support apparatus that includes: a site region extracting device which obtains a tomographic image which is picked up by a medical image diagnosing apparatus and extracts a predetermined site region from the obtained tomographic image; a first region extracting device which extracts a first lesion candidate region from the site region based on pixel values of the site region extracted by the predetermined site region extracting device; a second region extracting device which extracts a second lesion candidate region from the site region based on a distribution of the pixel values of the site region extracted by the predetermined site region extracting device; and a region correcting device which corrects the first lesion candidate region extracted by the first region extracting device by using the second lesion candidate region extracted by the second region extracting device.

In another aspect, there is provided an image processing program that enables a computer to execute: a reading step for reading a tomographic image picked up by a medical image diagnosing apparatus; a site region extracting step for extracting a predetermined site region from the obtained tomographic image; a first region extracting step for extracting a first lesion candidate region from the site region based on pixel values of the site region extracted in the predetermined site region extracting step; a second region extracting step for extracting a second lesion candidate region from the site region based on a distribution of the pixel values of the site region extracted in the predetermined site region extracting step; a region correcting step for correcting the first lesion candidate region extracted in the first region extracting step by using the second lesion candidate region extracted in the second region extracting step; and a displaying step for displaying the first lesion candidate region.

Thus, the accuracy in extracting a lesion candidate region can be improved.

BRIEF DESCRIPTION OF THE DRAWINGS

FIG. 11 are schematic diagrams showing an example of a divided lung field region based on the bronchial tubes, FIG. 11(a) being a diagram showing an outside, FIG. 11(b) being a diagram showing an inside, and FIG. 11(c) being a diagram showing a diaphragm thereof;

DESCRIPTION OF SYMBOLS

10 . . . central processing unit (CPU)
11 . . . medical tomographic image pickup apparatus
12 . . . local area network (LAN)
13 . . . magnetic disk
14 . . . main memory
15 . . . controller
16 . . . mouse
17 . . . key board
18 . . . display memory
19 . . . display
20 . . . printer

BEST MODE FOR CARRYING OUT THE INVENTION

Figure 1:
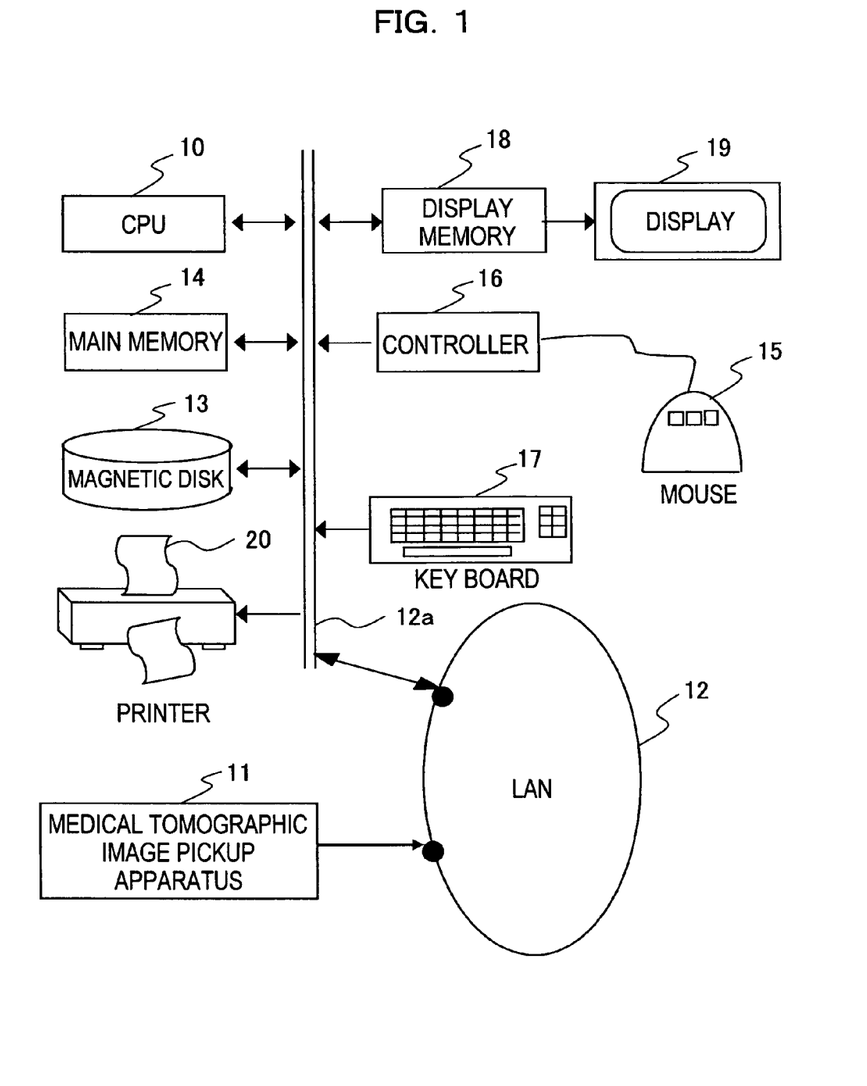
FIG. 1 is a block diagram showing a structure of a medical image diagnosing support apparatus of the present invention.

A medical image diagnosing support apparatus includes a central processing unit (CPU) 10, a medical tomographic image pickup apparatus 11, a magnetic disk 13, a main memory 14, a mouse 15 and a mouse controller 16, a key board 17, a display memory 18, a CRT display 19, a printer 20, local area network (LAN) 12 and a common bus 12a for electrically connecting each of the above components.

The CPU 10 controls the operation of each of the above components. The medical tomographic image pickup apparatus 11 is a medical image diagnosing apparatus such as an X-ray CT apparatus, a magnetic resonance imaging apparatus, an ultrasound image diagnosing equipment, and a nuclear medical apparatus which can measure tomographic images of an object to be examined. The LAN 12 means not only a short-range network, but also the one which enables a connection to various communication networks such as the Internet and a telephone line, and allows sending and receiving of image data between the apparatus and the other computer or a data base. The magnetic disk 13 stores a plurality of tomographic image data of patients, operation programs, and the like. The main memory 14 stores control programs for the medical image diagnosing support apparatus. The mouse 15 and the mouse controller 16 are used to manipulate soft switches on a screen. The key board 17 is used to set various parameters. The display memory 18 temporarily stores image data for displaying. The CRT display 19 displays images based on the image data obtained from the display memory 18. The printer 20 outputs a report as a diagnostic imaging result, for example.

In this embodiment, only the magnetic disk 13 is connected to the apparatus as a memory unit other than the main memory 14, but a FDD, a hard disk drive, a CD-ROM drive, an optical magnetic disk (MO) drive, a ZIP drive, a PD drive, and a DVD drive may be connected as well.

Figure 2:
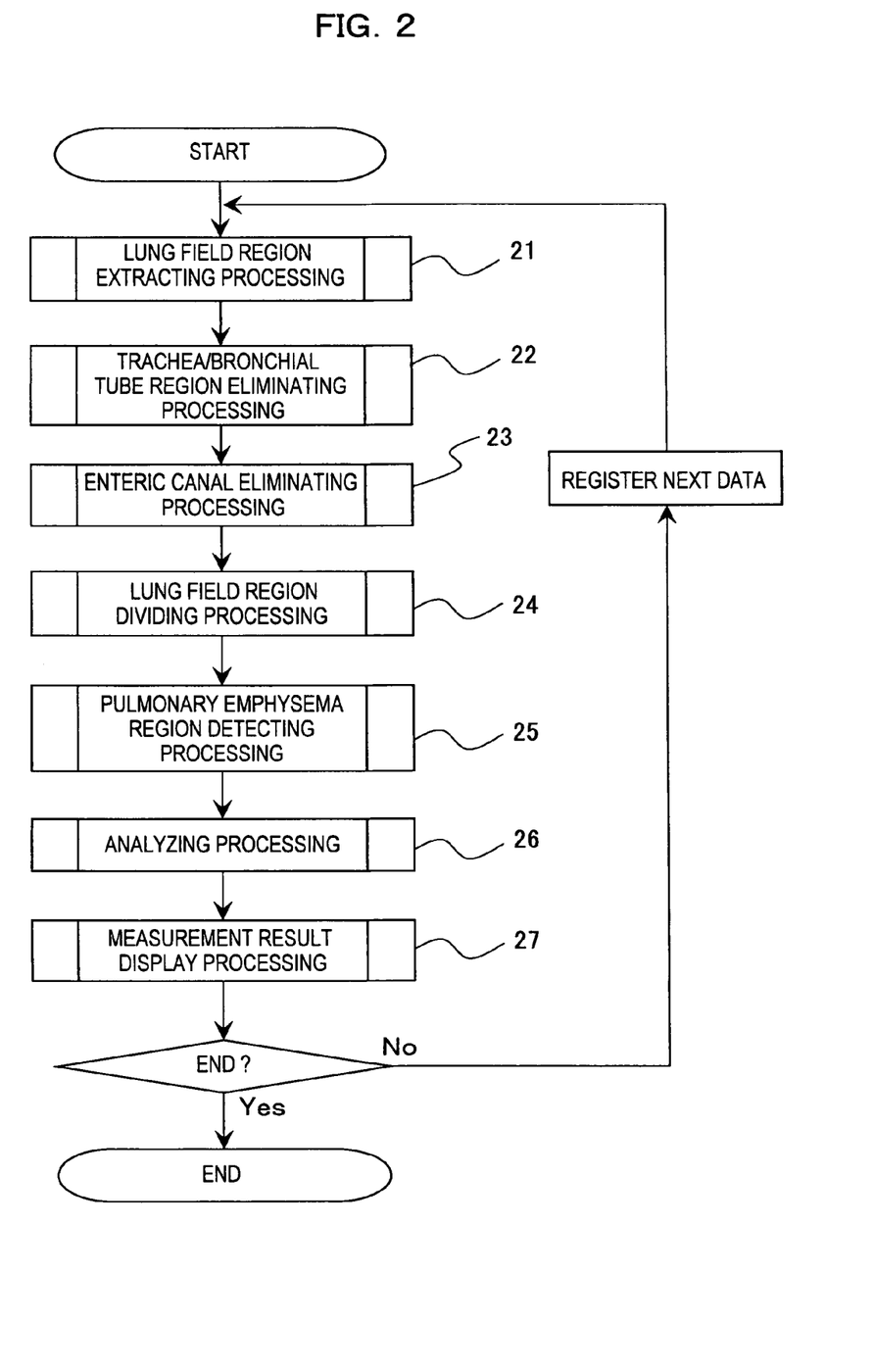
FIG. 2 is a flow chart showing an example of operation procedures of the medical image diagnosing support apparatus of FIG. 1.

Operations of the diagnostic image diagnosing support apparatus of FIG. 1 will be explained below with reference to the drawings. FIG. 2 is a diagram showing a main flow executed by the diagnostic imaging assistant apparatus of FIG. 1. The CPU 10 of FIG. 1 operates in accordance with the main flow. Now, the main flow will be explained in detail in the order of the steps therein.

First, when a screen to input an ID of an object to be examined is displayed on the display 19 of the medical image diagnosing support apparatus, an operator inputs an ID number of a patient. Then, a target tomographic image to be diagnosed which corresponds to the patient ID number among tomographic images picked up in advance by the medical tomographic image pickup apparatus 11 is read out from the magnetic disk 13.

[Step S21]

Figure 3:
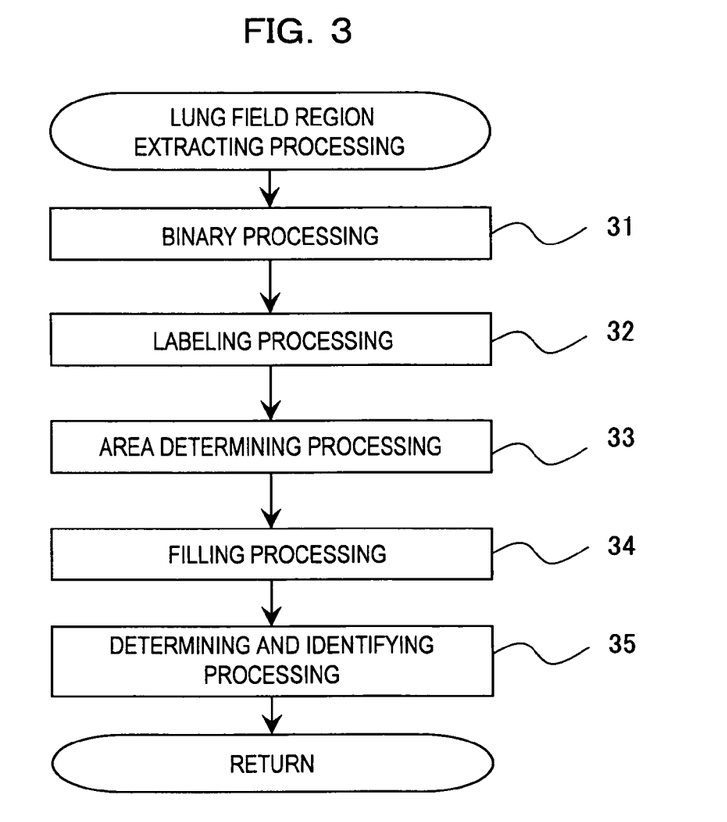
FIG. 3 is a flow chart showing a lung field region extracting processing at step 21 of FIG. 2.

The CPU 10 calls a subroutine to perform a lung field region extracting processing to the read out tomographic image. FIG. 3 is a flow chart showing the subroutine for the lung field region extracting processing at step 21. Now, the lung field region extracting processing will be explained in detail in the order of the steps therein.

[Step S31]

A threshold processing is applied to the read out tomographic image to generate a binary image. A threshold at this point is set to be a value which distinctly separate target regions to be calculated. Alternatively, a CT value for the highest frequency in the range of CT values of the tomographic image may be set to the median to calculate the lower limit and the upper limit of the range of CT values so that the calculated thresholds can be set to be the lower limit and the upper limit of the range of CT values.

[Step S32]

A labeling processing for individual identification is applied to the binary image generated at Step S30, to generate a two-dimensional label image.

[Step S33]

A label region having the largest area is extracted as a target region to be calculated from the label image which is two-dimensionally generated at Step S32.

[Step S34]

A filling processing is applied to a missing part between adjacent regions in the target region to be calculated at Step S33 to generate a body region.

[Step S35]

A determination identification processing is applied to the region extracted at Step S33 and the body region generated at Step S34 to extract a lung field region. Then the processing goes to step 22 of FIG. 2 in the main routine.

[Step S22]

Figure 4:
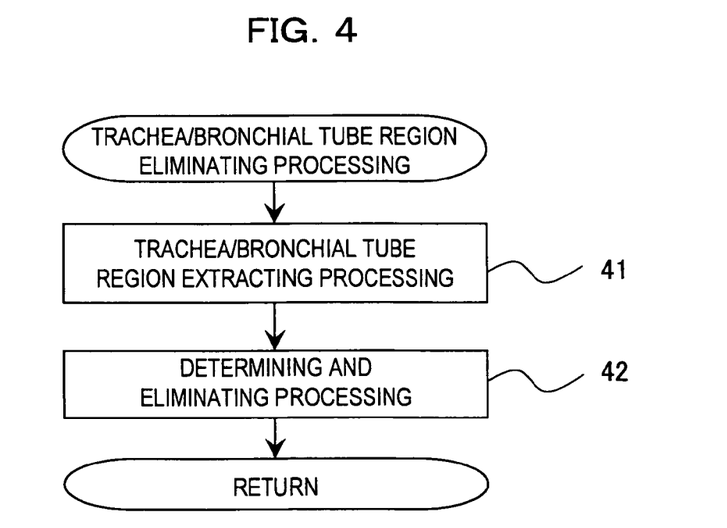
FIG. 4 is a detailed diagram showing a trachea/bronchial tube region eliminating processing at step 22 of FIG. 2.

Next, a subroutine is called to a perform trachea/bronchial tube region eliminating processing. FIG. 4 is a diagram showing a subroutine for the trachea/bronchial tube region eliminating processing at step 22.

Now, the trachea/bronchial tube region eliminating processing will be explained in detail in the order of the steps therein.

[Step S41]

The trachea/bronchial tube region is eliminated from the lung field region extracted at Step S21 by utilizing the characteristic shape of the trachea/bronchial tube region. This processing may be performed by eliminating small regions which are isolated in the lung field region around its centroid from the lung field region of each tomographic image.

[Step S42]

The parts of the trachea/bronchial tube region extracted at Step S41 which are overlapped with the lung field region extracted at Step S21 are eliminated. Then the processing goes to step 23 of FIG. 2 in the main routine.

[Step S23]

Figure 5:
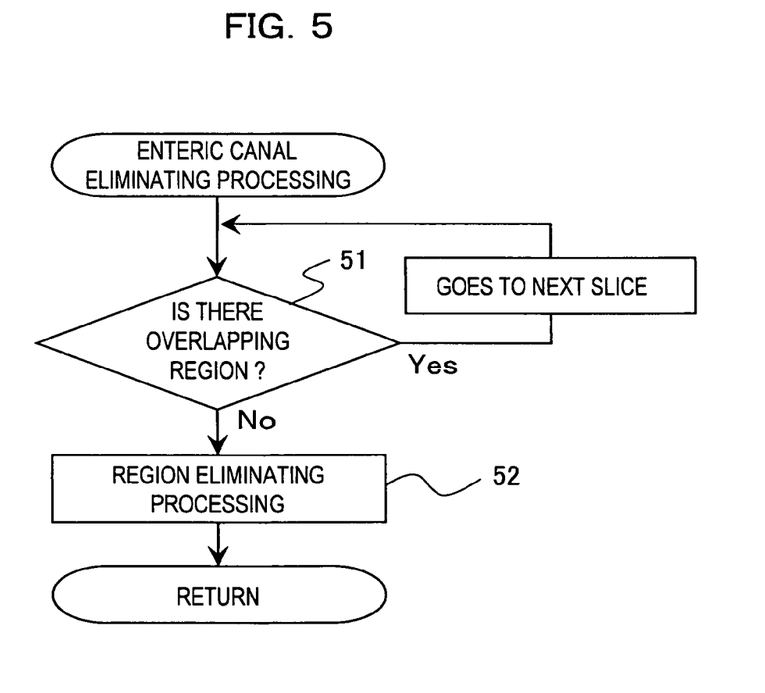
FIG. 5 is a detailed diagram showing an enteric canal region eliminating processing at step 23 of FIG. 2.

Next, a subroutine is called to perform an enteric canal eliminating processing. In this processing, a part where the lung field is in contact with the diaphragm is eliminated since the contacting part is influenced by the intestine. In this processing, the centroid of the lung field region extracted at Step S21 and Step S22 is set to be the starting point, and the processings of FIG. 5 are performed. FIG. 5 is a flow chart showing the subroutine for the enteric canal eliminating processing at step 23. Now, the enteric canal eliminating processing will be explained in detail in the order of the steps therein.

[Step S51]

It is determined if there is a lung field region at the same position between the axial slices, in the lung field region extracted at Step S21 and Step S22. When there is an overlapped lung field region, the next slice is processed. When there is no overlapped lung field region, the processing goes to Step S52.

[Step S52]

The region having no overlap between the axial slices is eliminated. Then the processing goes to step 24 of FIG. 2 in the main routine.

Alternatively, instead of the processings in FIG. 5, the region extracting method which is disclosed in Japanese Patent No. 2845995 in accordance with Japanese Patent Law may be used.

[Step S24]

Figure 6:
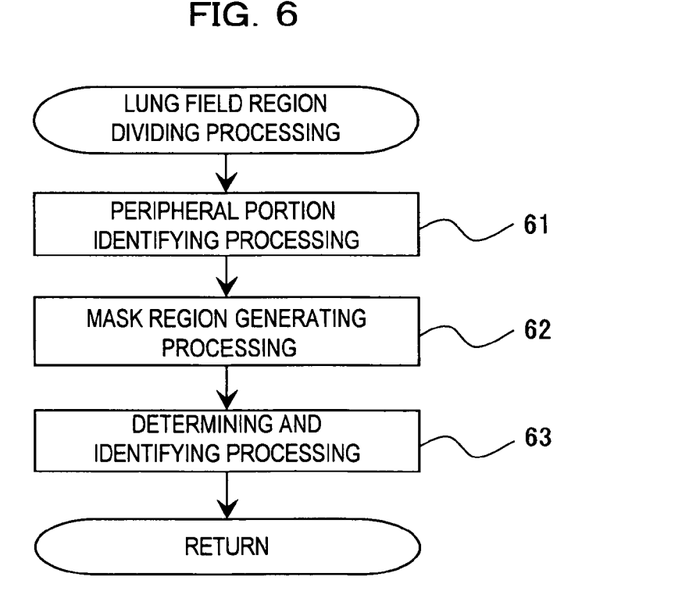
FIG. 6 is a detailed diagram showing a lung field region dividing processing at step 24 of FIG. 2.

Next, a subroutine is called to perform a lung field region dividing processing. In this processing, the lung field may be divided into upper right/middle/lower lung fields, or upper right/lower lung fields, but the lung field may be divided into the inner and outer parts in each tomographic image. FIG. 6 is a flow chart showing the subroutine for the lung field region dividing processing at step 24. Now, the lung field region dividing processing will be explained in detail in the order of the steps therein.

[Step S61]

In the lung field region extracted at steps S21 to S23, the peripheral portion of the lung field region extracted in each tomographic image is identified.

[Step S62]

A circle region around the pixel at the peripheral portion identified at Step S61 is set to be a mask region. The radius of the region is set to be 2 cm as an initial value, but may be set to be any value by an operator.

[Step S63]

A processing for discriminating and identifying between the lung field region extracted at steps S21 to S23 and the mask region set at Step S62 is performed. The part of the lung field region which is overlapped with the mask region is set to be a lung field outside region, while the part of the lung field region which is not overlapped with the mask region is set to be a lung field inside region. Then the processing goes to step 25 of FIG. 2 in the main routine.

[Step S25]

Figure 7:
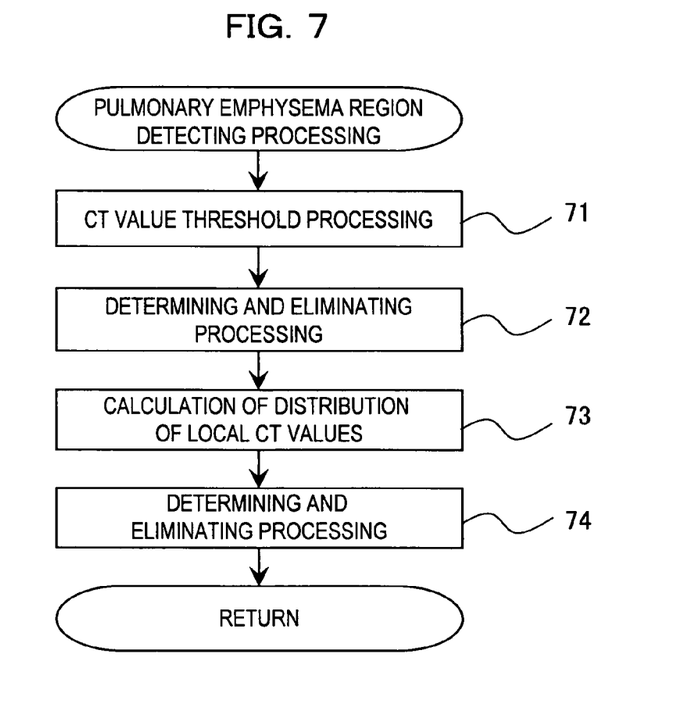
FIG. 7 is detailed diagram showing a pulmonary emphysema region extracting processing at a step 25 of FIG. 2.

Next, a subroutine is called to perform a pulmonary emphysema region detecting processing. FIG. 7 is a flow chart showing the subroutine for the pulmonary emphysema region detecting processing at step 25. Now, the pulmonary emphysema region detecting processing will be explained in detail in the order of the steps therein.

[Step S71]

A threshold processing is applied to the lung field region extracted at steps S21 to S23 to generate a binary image. The threshold in this processing is set to be −910 which is lower than a mean CT value in the lung field of a normal object to be examined. Alternatively, a threshold may be set based on an analysis result obtained by using a discriminant analysis method.

[Step S72]

From the pulmonary emphysema region extracted at Step S71, regions having a diameter of less than 3 mm which are believed to be the alveoli are eliminated.

[Step S73]

Figure 8:
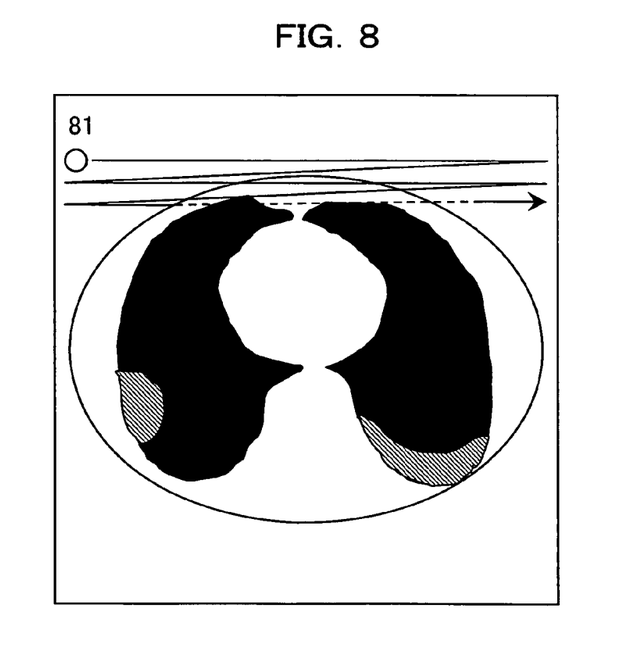
FIG. 8 is a diagram illustrating a processing for calculation of the difference of local CT values, which is a part of the analyzing processing at step 26 of FIG. 2.

For the lung field region extracted at steps S21 to S23, a distribution of the CT values in the target region 81 of FIG. 8 is calculated, and by using the distribution information, a threshold processing is performed.

The above distribution of the CT values is calculated by using at least one of the area ratio, the mean ratio, and the standard deviation ratio of the predetermined site region and the lesion candidate region.

The area ratio can be obtained most easily only by counting the number of pixels in each region, and the mean ratio and the standard deviation ratio can improve the accuracy in detecting a lesion candidate region more than the area ratio because the mean ratio and the standard deviation ratio use pixel values of the region. A combination of the area ratio, the mean ratio, and the standard deviation ratio can further improve the accuracy in detecting a lesion candidate region.

The distribution of the CT values may be calculated by dividing the lung field region in at least two parts and using at least one of the area ratio, the mean ratio, and the standard deviation of the divided predetermined site regions and the pulmonary emphysema region. This allows the area ratio, the mean ratio, and the standard deviation to be calculated based on the local pixel values of the divided regions, so that a detailed adjustment for the accuracy in detecting a lesion candidate region can be achieved compared to the case in which the entire site region is used.

[Step S74]

Only the part of the region extracted at Steps S71 and S72 which is overlapped with the region extracted at Step S73 is extracted. Then the processing goes to step 26 of FIG. 2 in the main routine.

[Step S26]

Next, a subroutine is called to perform an analyzing processing. Based on the information of the lung field region extracted at Steps S21 to S23, the lung field region divided at Step S24, and the pulmonary emphysema region extracted at Step S25, on a per tomographic image basis, the area, the mean value, the standard deviation, and the upper limit and lower limit of the 95% confidence interval relative to the mean value of the lung field region, and the area, the mean value, the standard deviation, and the upper limit and lower limit of the 95% confidence interval relative to the mean value of the pulmonary emphysema region are calculated to form pairs with the corresponding values. Similarly, on an entire lung field and each lung field unit basis, analysis results are calculated. In this embodiment, the range of confidence interval relative to the means value is initially set to 95%, but may be set to any other percentage by an operator.

[Step S27]

Figure 9:
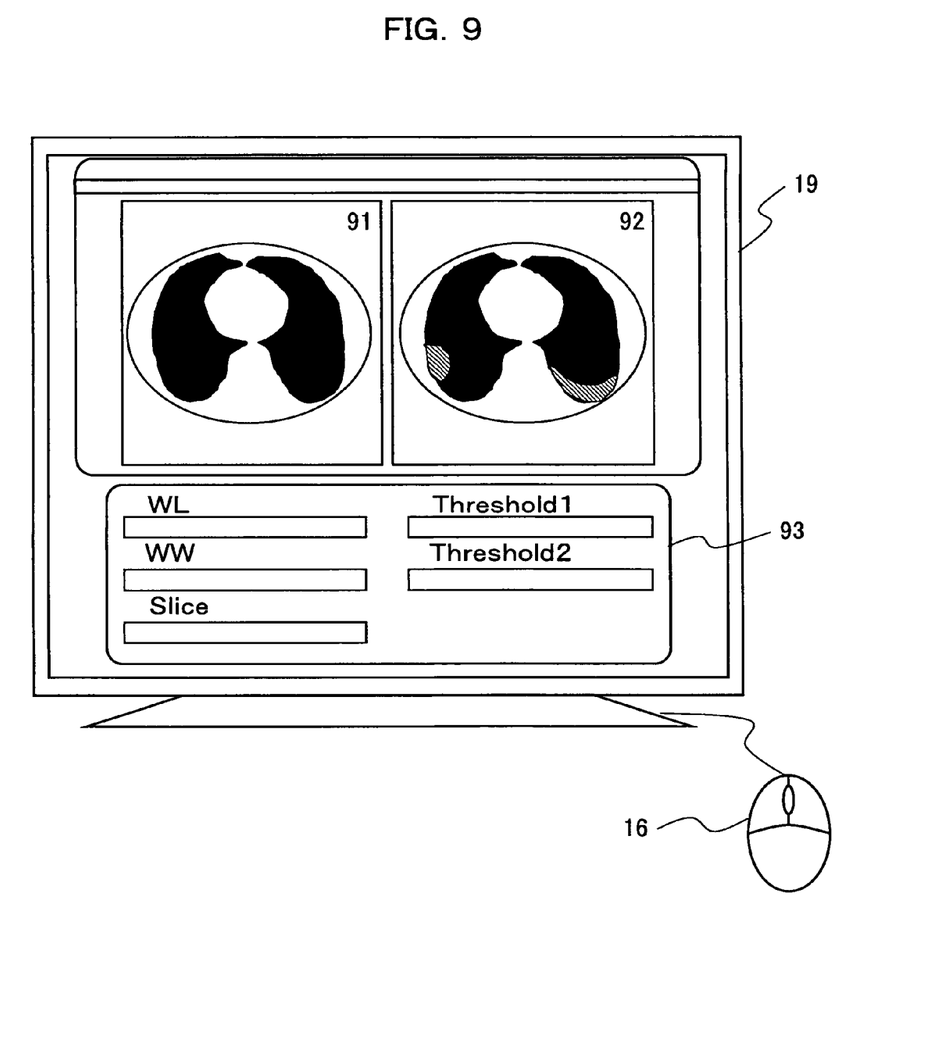
FIG. 9 is a diagram showing an example of a screen which displays a measurement result.
Figure 10:
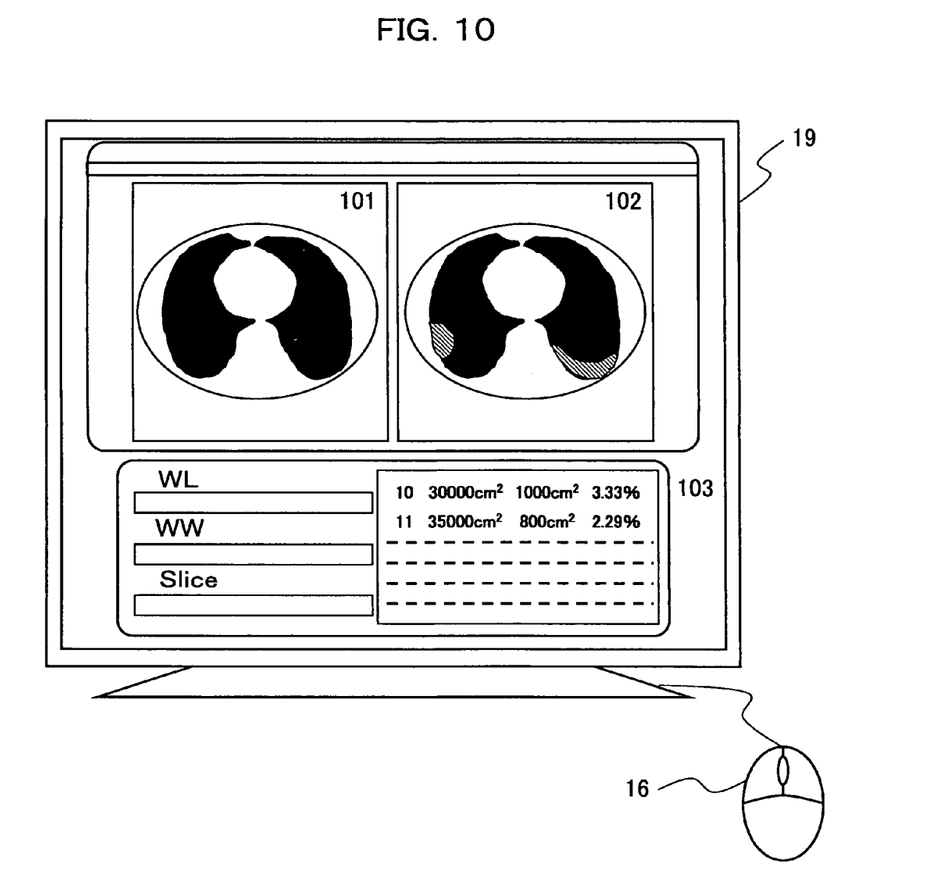
FIG. 10 is a diagram showing an example of a screen which displays a measurement and analysis result which is different from the one of FIG. 9.

Next, a measurement result displaying processing is executed. Based on the analysis result for the entire lung field at Step S26, the pulmonary emphysema region is displayed in a different color. FIG. 9 is a diagram showing an example of a screen at this point. A screen 91 shows a read-in tomographic image. A screen 92 shows a display image of a measurement result. In FIG. 9, a display screen 93 is provided to display the conditions for picking up the above described tomographic images, but the display screen 93 is not essential, and the screens 91 and 92 may be the only displayed contents. In this embodiment, an example in which the screens 91 and 92 are displayed in two screens is presented, but an image in which the tomographic image and the pulmonary emphysema region are overlapped may be displayed in one screen. FIG. 10 is a diagram showing an example of a screen which displays an analysis result.

A screen 101 displays a read-in tomographic image, a screen 102 displays a display image of a measurement result, and a screen 103 displays analysis results. The screen 103 of FIG. 10 displays, as analysis results, the measured areas "30000 $cm^2$, 1000 $cm^2$" for each pulmonary emphysema region, and the percentage "3.33%" of the pulmonary emphysema region relative to the entire lung field region. This clearly provides a lesion candidate region in high accuracy to doctors.

In the above display, the tomographic image and the lesion candidate region may be superimposed to be displayed.

This enables a diagnosis to be intuitively made on the position relationship between the tomographic image and the lesion candidate region.

Alternatively, in the above display, the lesion candidate region may be displayed next to the tomographic image.

This allows the pixel value of the tomographic image which would be hidden in the superimposed display to be analyzed.

Alternatively, in the above display, a soft switch for switching between display/non-display modes of the lesion candidate region may be displayed on the display screen so that the display can be selected using a pointing device. This enables an operator to select only the tomographic image to be displayed for diagnosis, or both of the tomographic image and the lesion candidate region to be displayed.

Alternatively, the analysis results for each tomographic image such as those shown as the reference numeral 103 in FIG. 10 may be displayed as a list. The results in the list may be output to a printer 20 to be provided to a patient to use it as an instruction tool for stop smoking and the like. Or a pop-up window may be displayed by specifying a lesion candidate region using a mouse 16 so that information of a characteristic amount and a position of the lesion candidate region is displayed in the pop-up window. An example of this display will be explained below with reference to FIG. 11 and FIG. 12.

Figure 11A:
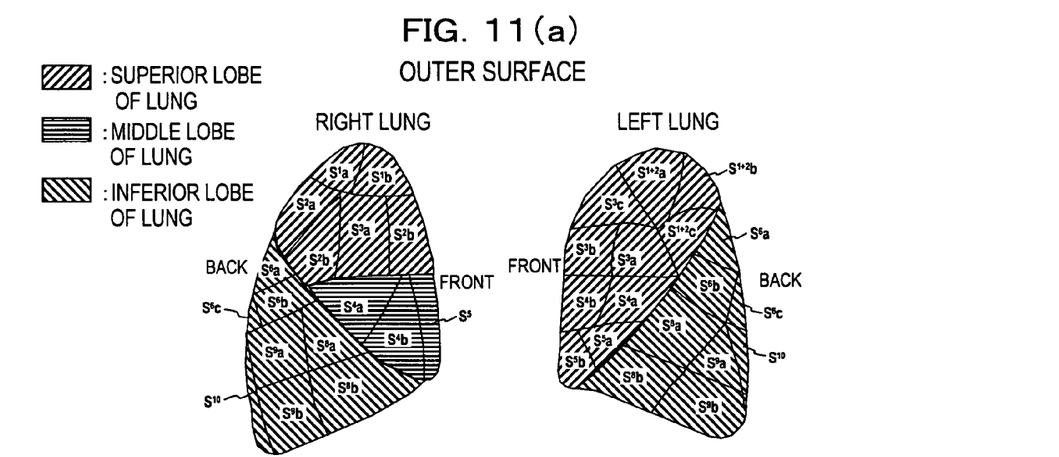
Figure 11B:
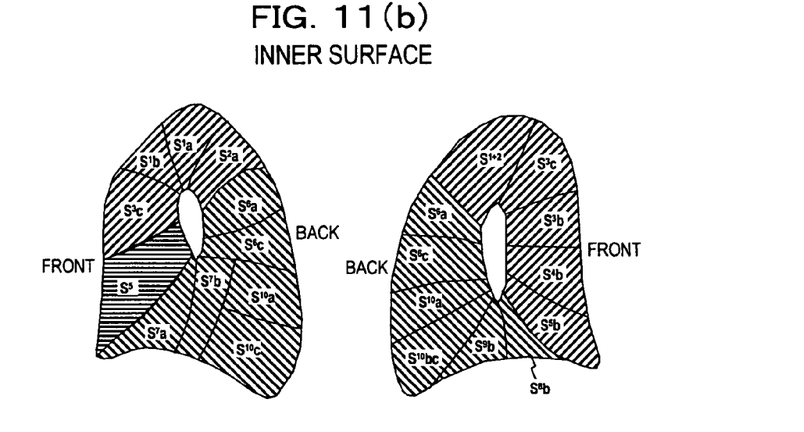
Figure 11C:
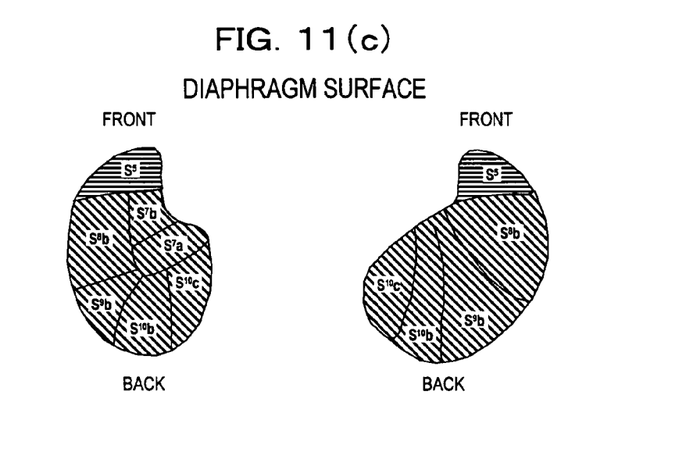
Figure 12:
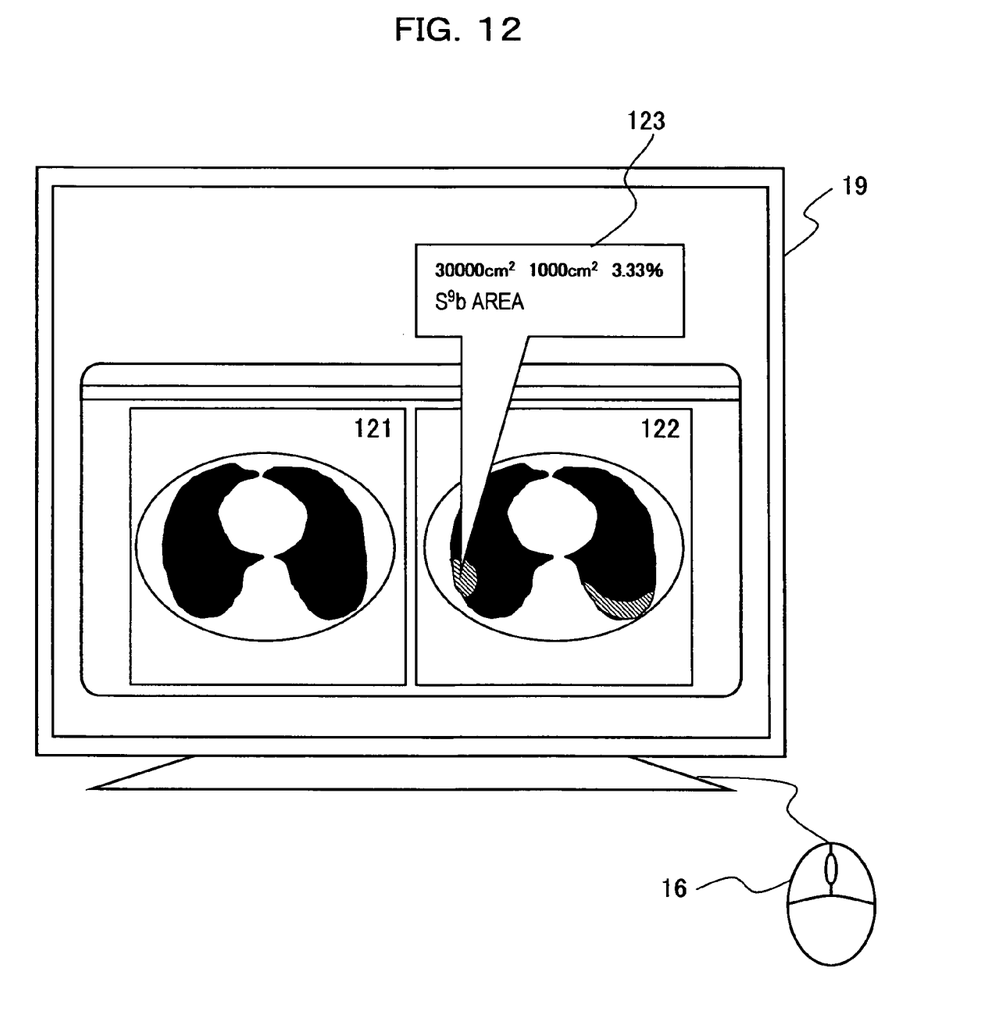
FIG. 12 is a diagram showing an example of a screen which displays a measurement result.

FIG. 11 is a schematic diagram showing an example of a divided lung field region based on the bronchial tubes. The areas with lines running diagonally from bottom left to top right represent superior lobe regions of the lung, the area with horizontal line represent middle lobe regions of the lung, and the areas with lines running diagonally from bottom right to top left represent inferior lobe regions of the lung. The reference numerals "$S^1$", "$S^2$" . . . are identification numbers given to identify bronchial tubes. The reference numerals "$S^1a$", "$S^1b$" . . . are given to show regions around the main bronchial tubes. FIG. 12 is an example of a display screen, and a screen 121 shows a tomographic image, a screen 122 shows a display image of a measurement result, and a screen 123 shows a pop-up window.

The medical image diagnosing support apparatus stores the information of the regions around the bronchial tubes shown in FIG. 11 in a magnetic disk 23 in advance. Based on the lung region extracted at Step S21 and the information of the regions around the bronchial tubes shown in FIG. 11, it is determined in which one of the regions around the bronchial tubes "$S^1a$", "$S^1b$" . . . the pulmonary emphysema region is located, and the obtained result is recorded as position information of the pulmonary emphysema region. The position information of the pulmonary emphysema region is not limited to that of the regions around the bronchial tubes, and may be that relative to the superior lobe region, the middle lobe region, and the inferior lobe region.

When an operator clicks the pulmonary emphysema region displayed on the display 19 using the mouse 16, the pop-up window 123 of FIG. 12 is displayed. The pop-up window 123 includes the displays of the characteristic amounts "30000 $cm^2$, 1000 $cm^2$, 3.33%" of the pulmonary emphysema region which is specified by clicking with the mouse 16, and the position "$S^9b$ area" of the pulmonary emphysema region. The information displayed in the pop-up window 103 may include only one of the characteristic amount and the position information, or may include other information. This allows an operator to select only a tomographic image or both of a tomographic image and a lesion candidate region to be displayed for diagnosing.

This embodiment includes: the extracting step 21 for obtaining a tomographic image which is picked up by the medical tomographic image pickup apparatus 11, and extracting a predetermined site region from the obtained tomographic image; the steps 22 to 24 for extracting a first lesion candidate region from the site region based on pixel values of the site region extracted in the predetermined site region extracting step; the step 25 for extracting a second lesion candidate region from the site region based on a distribution of pixel values of the extracted site region; and the step 26 for correcting the first lesion candidate region extracted in the first region extracting step by using the extracted second lesion candidate region.

These steps enable any extraction errors occurred in a lesion candidate region which are caused by individual differences such as a body type of objects to be examined to be corrected.

Figure 13:
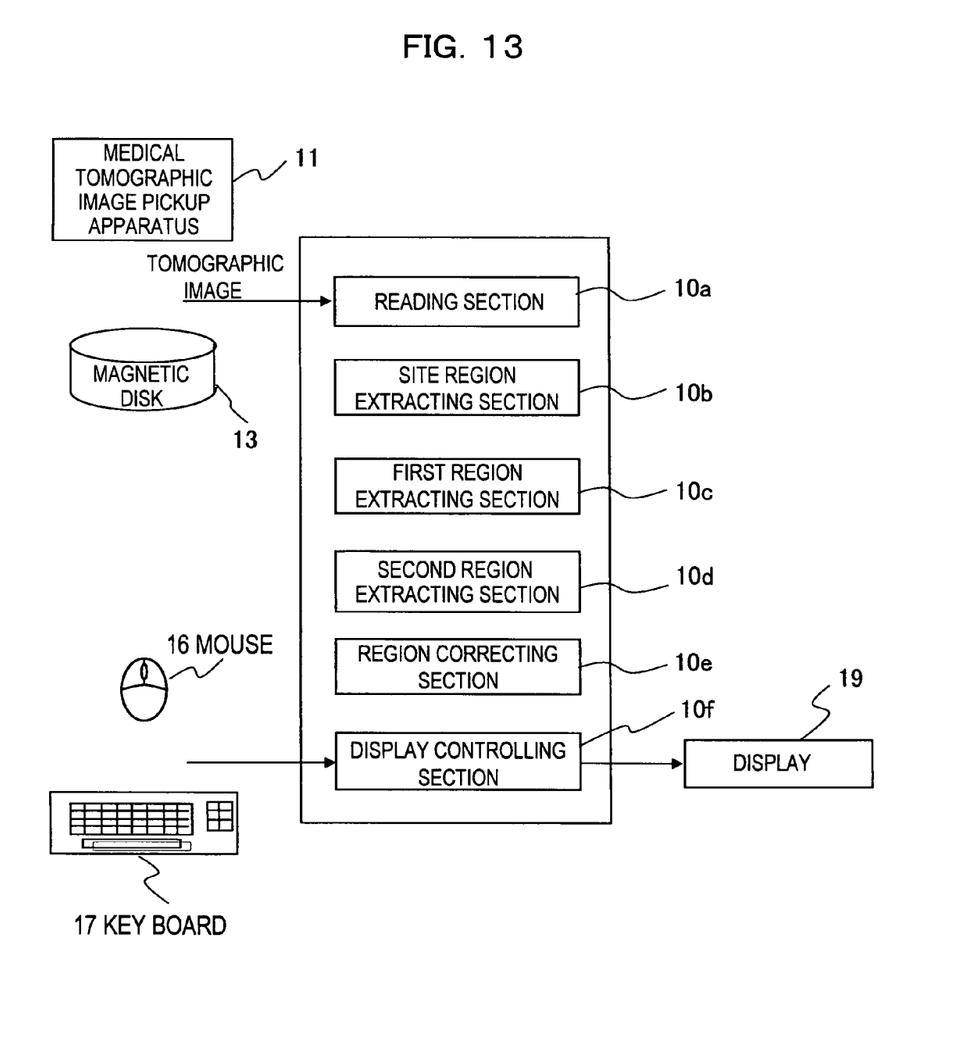
FIG. 13 is a block diagram showing a structure of an image processing program.

FIG. 13 is a block diagram showing an image processing program.

The image processing program includes: a reading section for reading a tomographic image from an image database which is connected via the medical tomographic image pickup apparatus 11, the magnetic disk 23, or the LAN 12; a site region extracting section 10b for extracting a predetermined site (for example, lung region) from the read-in tomographic image; a first region extracting section 10c for extracting a first lesion candidate region from the predetermined site region based on pixel values of a predetermined site region; a second region extracting section 10d for extracting a second lesion candidate region from the predetermined site region based on pixel values of the predetermined site region; a region correcting section 10e for correcting the first lesion candidate region by using the second lesion candidate region; and a display controlling section 10f for displaying the first lesion candidate region. The display controlling section 10f controls displays on the screen 103 of FIG. 10 which displays analysis results and displays in the pop-up window 123 of FIG. 12 in response to instructions which are input via the mouse 15 or the key board 17. The medical diagnostic imaging assistant apparatus stores the image processing program shown in FIG. 13 into the magnetic disk 23, and the CPU 10 conveniently loads the program onto the main memory 14 to execute it. In this way, the operation processings of the above embodiment are executed.

In the above embodiment, various processings are performed based on tomographic images which are read in, but similar processings can be performed based on projection images which are picked up by using X-ray diagnostic apparatuses or DR apparatuses as well as the tomographic images.

INDUSTRIAL APPLICABILITY

The present invention can be applied to not only to image processings based on medical images but also to a general technology for processing images in which a first pixel values region and a second pixel values region are extracted from images which are read in advance, and the first pixel values region is corrected based on the second pixel values region.

The invention claimed is:

1. A medical image diagnosing support method, comprising:
 a site region extracting step of obtaining, by a medical image diagnosing apparatus, a tomographic image, and extracting a predetermined site region from the obtained tomographic image;
 a first region extracting step of extracting a first lesion candidate region from the site region in the tomographic image based on pixel values of the site region extracted in the predetermined site region extracting step;
 a second region extracting step of extracting a second lesion candidate region from the site region in the tomographic image based on a distribution of pixel values of the site region extracted in the predetermined site region extracting step; and
 a region correcting step of extracting as a pulmonary emphysema a corrected lesion candidate region where the first lesion candidate region overlaps with the second lesion candidate region.

2. The medical image diagnosing support method according to claim 1, wherein the distribution of the pixel values of the predetermined site region is calculated by using at least one of an area ratio, a mean ratio, and a standard deviation ratio of the predetermined site region and the first lesion candidate region.

3. The medical image diagnosing support method according to claim 1, wherein the distribution of the pixel values of the predetermined site region is calculated by dividing the extracted predetermined site region into at least two parts, and using at least one of an area ratio, a mean ratio, and a standard deviation ratio of the divided predetermined site region and the first lesion candidate region.

4. The medical image diagnosing support method according to claim 3, wherein the division of the predetermined site region includes a division into a number of parts, the number depending on the predetermined site region.

5. The medical image diagnosing support method according to claim 1, further comprising:
 a progression calculating step of calculating a progression of the first lesion candidate region which is corrected in the region correcting step; and
 a displaying step of changing a color of the corrected first lesion candidate region depending on the progression of the overlapped lesion candidate region calculated in the progression calculating step, and displaying the overlapped lesion candidate region having the changed color in association with the tomographic image.

6. The medical image diagnosing support method according to claim 5, wherein, in the displaying step, the tomographic image is displayed superimposed on the overlapped region.

7. The medical image diagnosing support method according to claim 5, wherein, in the displaying step, the overlapped region is displayed next to the tomographic image.

8. The medical image diagnosing support method according to claim 5, wherein the displaying step includes a selecting step of selecting a display or non-display mode of the overlapped region.

9. A medical image diagnosing support apparatus comprising:
 a site region extracting device configured to obtain a tomographic image which is obtained by a medical image diagnosing apparatus and to extract a predetermined site region from the obtained tomographic image;
 a first region extracting device configured to extract a first lesion candidate region from the site region in the tomographic image based on pixel values of the site region extracted by the predetermined site region extracting device;
 a second region extracting device configured to extract a second lesion candidate region from the site region in the tomographic image based on a distribution of the pixel values of the site region extracted by the predetermined site region extracting device; and
 a region correcting device configured to extract as a pulmonary emphysema a corrected lesion candidate region where the first lesion candidate region overlaps with the second lesion candidate region.

10. The medical image diagnosing support apparatus according to claim 9, wherein the second region extracting device is configured to calculate the distribution of the pixel values of the predetermined site region by using at least one of an area ratio, a mean ratio, and a standard deviation ratio of the predetermined site region and the first lesion candidate region.

11. The medical image diagnosing support apparatus according to claim 9, wherein the second region extracting device is configured to calculate the distribution of the pixel values of the predetermined site region by dividing the extracted predetermined site region into at least two parts, and using at least one of an area ratio, a mean ratio, and a standard deviation ratio of the divided predetermined site region and the first lesion candidate region.

12. The medical image diagnosing support apparatus according to claim 11, wherein the division of the predetermined site region includes a division into a number of parts, the number depending on the predetermined site region.

13. The medical image diagnosing support apparatus according to claim 9, further comprising:
 a progression calculating device which calculates a progression of the lesion candidate region corrected in the region correcting step; and
 a displaying device configured to change a color of the overlapped region depending on the progression of the overlapped region calculated by the progression calculating device, and to display the overlapped region having the changed color in association with the tomographic image.

14. The medical image diagnosing support apparatus according to claim 13, wherein, by the displaying device, the tomographic image is displayed superimposed on the overlapped region.

15. The medical diagnostic imaging assistant apparatus according to claim 13, wherein, by the displaying device, the overlapped region is displayed next to the tomographic image.

16. The medical image diagnosing support apparatus according to claim 13, wherein the displaying device includes a selecting device for selecting a display or non-display mode of the overlapped region.

17. The medical image diagnosing support apparatus according to claim 13, further comprising a position coordinate input device configured to specify a position coordinate on a screen which is displayed by the displaying device, and when the lesion candidate region is specified by the position coordinate input device, the displaying device is configured to display another screen which is different from the currently displayed screen, and to display at least one of a characteristic amount of the lesion candidate region and position information of the lesion candidate region in the another screen.

18. The medical image diagnosing support apparatus according to claim 9, wherein the tomographic image is obtained by obtaining an image of a lung field region of an object to be examined, and the overlapped region is a pulmonary emphysema region included in the lung field region.

19. The medical image diagnosing support apparatus according to claim 18, wherein the first region extracting device is configured to extract a pulmonary emphysema region, the second extracting device is configured to extract an alveolus region, the region correcting device is configured to correct by eliminating the alveolus region from the pulmonary emphysema region.

20. A non-transitory computer readable medium tangibly embodying an image processing program of instructions executable by a computer to execute:

a reading step of reading, by a medical image diagnosing apparatus, a tomographic image;

a site region extracting step of extracting a predetermined site region from the obtained tomographic image;

a first region extracting step of extracting a first lesion candidate region from the site region in the tomographic image based on pixel values of the site region extracted in the predetermined site region extracting step;

a second region extracting step of extracting a second lesion candidate region from the site region in the tomographic image based on a distribution of the pixel values of the site region extracted in the predetermined site region extracting step;

a region correcting step of extracting as a pulmonary emphysema a corrected lesion candidate region where the first lesion candidate region extracted in the first region overlaps with the second lesion candidate region; and a displaying step of displaying the corrected lesion candidate region as the pulmonary emphysema.

* * * * *